United States Patent [19]

Shander et al.

[11] Patent Number: 5,143,925
[45] Date of Patent: Sep. 1, 1992

[54] ALTERATION OF RATE AND CHARACTER OF HAIR GROWTH

[76] Inventors: Douglas Shander, 16112 Howard Landing Dr., Gaithersburg, Md. 20878; Margaret G. Funkhouser, 1332 S. Pollard St., Arlington, Va. 22204

[21] Appl. No.: 794,321

[22] Filed: Nov. 12, 1991

Related U.S. Application Data

[63] Continuation of Ser. No. 632,126, Dec. 20, 1990, abandoned.

[51] Int. Cl.[5] .............................................. A61K 31/42
[52] U.S. Cl. .................................................. 514/378
[58] Field of Search ........................ 514/340, 380, 378

[56] References Cited

U.S. PATENT DOCUMENTS

| | | | |
|---|---|---|---|
| 4,720,489 | 1/1988 | Shander | 514/171 |
| 4,885,289 | 12/1989 | Breuer et al. | 514/170 |
| 4,912,120 | 3/1980 | Castelhano et al. | 514/380 |
| 4,929,630 | 5/1990 | Castelhano et al. | 514/380 |

OTHER PUBLICATIONS

Hattori, M. et al., J. Dermatology 10(1): 45–54, 1983.
Martinet, N. et al., J. Biol. Chem. 263(9): 4236–4241, 1988.
Ogawa, H. et al., Curr. Prob. Dermatol. 11 (Norm Abnorm Epidermal Differ): 159–170, 1983.
Orfanos, C. et al. (Ed.), Hair Research, Springer-Verlag, 1981.
Folk et al., *Adv. Enzymol.*, 38: 109–191 (1973).
Ogawa, et al., *J. Invest. Dermatol.*, 68: 32–35 (1977).
Chung, et al., *Proc. Natl. Acad. Sci.*, U.S.A. 69: 303–307 (1972).
Peterson et al., *Biochim. Biophys. Acta*, 11: 2858–2863 (1972).
Harding, et al., *Biochemistry*, 11: 2858–2863 (1972).
Harding et al., *Biochemistry*, 10,(4): 624–630, (1971).
Goldsmith, L. A., "Hair Follicle Transglutaminases and the Formation of-(Glutamyl) Cross Links in Hair Research", pp. 290–335, (1981) Ed. by Orfanos Montagna, and Stuttgen.
Hattori, et al., *J. of Dermatology*, 10: 45–54 (1983).
Richards et al., *Cancer Research*, 42: 4143–4152 (1982).
DeYoung et al., *Cancer Research*, 38: 3697–3701 (1978).
Chase, *Physiolo. Zool.*, 24: 1–8 (1951).
Killackey et al., *Molecular Pharmacology*, 35,5: 701–706 (1989).
Scott et al., *Transactions*, 15: 1167–1168 (1987).
Straile, Biology of the Skin and Hair Growth, pp. 35–57 (1965) ed. by Lyne and Short.

*Primary Examiner*—Frederick E. Waddell
*Assistant Examiner*—Diane Gardner
*Attorney, Agent, or Firm*—Fish & Richardson

[57] ABSTRACT

The rate and character of mammalian hair growth is altered by topical application to the skin of a composition containing an inhibitor of the enzyme transglutaminase.

6 Claims, No Drawings

ALTERATION OF RATE AND CHARACTER OF HAIR GROWTH

This is a continuation of application Ser. No. 07/632,126, filed Dec. 20, 1990, now abandoned.

This invention relates to a method for altering the rate and character of mammalian hair growth, particularly androgen-stimulated hair growth, by topical application to the skin of a composition containing an inhibitor of transglutaminase.

BACKGROUND OF THE INVENTION

The enzyme transglutaminase (TGase (R-glutamyl-peptide: amine gamma-glutamyl-transferase EC 2.3.2.13) has been reported to catalyze the formation of dipeptide bonds between the glutamine and lysine residues in polypeptides via covalent coupling of the gamma carboxyamide group of peptide bound glutamine residues with an epsilon amino group of peptide bound lysine residues (Folk, et al., *Adv. Enzymol.*, 38:109-191 (1973)). The TGase in hair follicles of humans is reported to be distinct from the epidermal TGase (Ogawa, et al., *J. Invest. Dermatol.*, 68:32-35 (1977)). TGase is also said to be found in hair follicles of guinea pigs (Chung, et al., *Proc. Natl. Acad. Sci.*, U.S.A. 69:303-307 (1972)); of rats (Peterson, et al., *Biochim. Biophys. Acta*, 657:268-276 (1981)); and of sheep (Harding, et al., *Biochemistry*, 11:2858-2863 (1972)).

In addition to direct detection of TGases in follicles, the dipeptide gamma-glutaminyl (lysyl) crosslinks have also been identified in the proteins of the medulla of the hair shaft and the inner root sheath of guinea pig follicle which adjoins the cortical cells of the hair (Harding, et al., *Biochemistry*, 10,(4):624-630 (1971). These dipeptide bonds are said to stabilize structural proteins imparting structural integrity to the medulla and to provide resistance to proteolytic attack by microorganisms (Goldsmith, L. A., "Hair Follicle Transglutaminases and the Formation of -(Glutamyl) Cross Links in Hair Research", pp. 290-35, 1981, Ed. by Orfanos Montagna, and Stuttgen, Springer Verlag Berlin Heidelberg).

The enzyme activity of TGase is reported to be increased in actively growing versus quiescent regions of hair growth (Hattori, et al., *J. of Dermatology*, 10:45-54 (1983)). It has not been known what impact, if any, inhibition of transglutaminase activity would have on the rate or character of hair growth since its activity on hair shaft proteins is confined to the latter stages of hair growth involving the secondary or posttranslational modifications of previously synthesized shaft proteins.

U.S. Pat. Nos. 4,912,120 and 4,929,630 Castelhano et al. describe various 3,5-disubstituted-4,5-dihydroisoxazoles as inhibitors of transglutaminase useful for administration to mammals suffering from a disease characterized by elevated transglutaminase activity, such as acne, psoriasis, or cataracts.

It has previously been proposed to alter the rate and character of hair growth by applying to the skin inhibitors of certain enzymes such as inhibitors of 5-alpha-reductase or of ornithine decarboxylase, or such antiandrogen materials as cytoplasmic androgen receptor binding agents, as described in U.S. Pat. Nos. 4,720,489 and 4,885,298. Moreover, it has been theorized that other enzymes, including gamma-glutamyl transpeptidase, are involved in various stages of hair follicle formation or of hair growth, but the relation between the various enzymes and the reactions which they control, as well as their effect upon each other and upon hair growth, has not been fully understood, as appears from Richards et al., *Cancer Research*, 42:4143-4152 (1982); DeYoung et al, *Cancer Research*, 38:3697-3701 (1978); and Chase, *Physiolo. Zool.*, 24:1-8 (1951).

It has now been found that topical application to the skin of a normal mammal (including human), i.e., a mammal free from a disease characterized by elevated transglutaminase activity, of a composition containing an inhibitor of transglutaminase, is effective to reduce the rate and alter the character of mammalian hair growth, particularly androgen-stimulated hair growth. By "alter the character" is meant that it renders the hair, particularly androgen-stimulated hair growth, softer and downier and/or more easily cut. Particularly preferred is a process in which the inhibitor is a specific, non-competitive inhibitor of transglutaminase such as 3-bromo-5-(N-benzyloxycarbonyl-1-phenylalanamidomethyl)-4,5-dihydroisoxazole (BBD) 5-(N-benzyloxycarbonyl-L-para-tyrosinamidomethyl)-3-bromo-4,5-dihydroisoxazole, 5-(N-2-(s)-6-methoxy-2-naphthyl)-propionyl)-L-p-tyrosinamidomethyl-5-(s) -3-bromo-4,5-dihydroisoxazole or other 3,5-disubstituted-4,5-dihydroisoxazole inhibitor as described in U.S. Pat. Nos. 4,912,120 and 4,929,630, the descriptions of which are hereby incorporated by reference in the present application.

The composition of the present invention contains, in addition to the inhibitor, a non-toxic dermatologically acceptable vehicle or carrier which is adapted to be spread upon the skin including the follicles. The concentration of the inhibitor in the composition may be varied over a wide range up to a saturated solution, preferably from 0.1 to 20% by weight or even more; the reduction of hair growth increases as the amount of inhibitor applied increases per unit area of skin. The maximum amount effectively applied is limited only by the rate at which the inhibitor penetrates the skin. Generally, the effective amounts range from 10 to 2500 micrograms or more per square centimeter of skin. In the case of BBD inhibitor, which is hydrophobic, non-aqueous vehicles, such as those based on an alcohol, e.g., ethyl alcohol or benzyl alcohol, are preferred.

The following specific example is intended to illustrate more clearly the nature of the present invention without acting as a limitation upon its scope.

EXAMPLE 1

A vehicle or carrier was prepared having the following composition:

|  | Percent by Volume |
| --- | --- |
| Acetone | 75% |
| Propylene Carbonate | 20% |
| Benzyl Alcohol | 5% |

The compound BBD was mixed with separate portions of the foregoing vehicle to provide specimens containing 1,2,5,10, and 20% by weight of the inhibitor respectively.

Five groups (seven or eight animals in each group) of male intact Golden Syrian hamsters were provided. These animals are considered acceptable models for human beard hair growth in that they display oval shaped flank organs, one on each side, each about 8 mm. in major diameter, which grow thick black and coarse hair similar to human beard hair. These organs produce hair in response to androgens in the hamster. The flank organs of each hamster were depilated by applying a thioglycolate-based chemical depilatory (Surgex), and to one organ of each animal was applied 10-25 μl. of vehicle alone once a day, while to the other organ of each animal was applied an equal amount of vehicle containing inhibitor. After 2 ½ weeks of such applications (five days a week for a total of eighteen days), the flank organs were shaved and the amount of recovered hair (hair mass) from each was weighed. The extent of reduction in hair growth by the inhibitor was expressed as the percent decrease in hair mass on the organ treated with inhibitor as compared to the organ treated with vehicle alone. As a control, one additional control group of eight animals had both flank organs of each animal treated with vehicle alone. The results were as shown in Table 1 below.

TABLE 1

Inhibition of Hair Mass by the Transglutaminase Inhibitor 5-(N-Benzyloxycarbonyl-L-phenylalaninamidomethyl)-3-bromo-4,5-dihydroisoxazole (BBD)

| Treatment | No. of Animals | Flank Organ Hair Mass (mg ± SEM) | | % Inhibition (+SEM) |
|---|---|---|---|---|
| | | Treated | Vehicle | |
| 1% BBD | 8 | 2.614 ± .19 | 3.289 ± .22 | 19.54 ± 6.07 |
| 2% BBD | 8 | 2.827 ± .23 | 2.881 ± .32 | −3.63 ± 9.91 |
| 5% BBD | 8 | 2.279 ± .28 | 3.021 ± .18 | 22.83 ± 9.62 |
| 10% BBD | 8 | 1.389 ± .12 | 3.207 ± .14 | 56.08 ± 4.64 |
| 20% BBD | 7 | .333 ± .06 | 2.743 ± .29 | 87.87 ± 1.54 |
| Control | 8 | 3.146 ± .24 | 3.239 ± .36 | −1.76 ± 6.98 |

Visual inspection of the hamsters during treatment showed that the inhibitor caused a decrease in the length of the hair dependent upon the concentration of the inhibitor. Microscopic examination of representative hair shafts harvested from the flank organs showed that treatment with the 20% concentration of BBD produced a dramatic deterioration of the hair shaft structure including disorganization of the medulla and cuticle; less dramatic but visually obvious changes in the medulla of hair shafts from organs treated with 5% and 10% concentrations were also observed. It was also found that the inhibiting effect of BBD on transglutaminase activity was dose related.

What is claimed is:

1. The process of reducing the rate of mammalian hair growth which comprises the step of applying to the skin of mammals free from a disease characterized by elevated transglutaminase activity a composition containing an inhibitor of transglutaminase at a dosage effective to reduce the rate of said hair growth.

2. The process as claimed in claim 1 in which said inhibitor is 5-(N-benzyl-oxycarbonyl-1-phenylalanamidomethyl) -3-bromo-4,5-dihydroisoxazole.

3. The process as claimed in claim 1 or 2 in which said dosage is from 10 to 2500 micrograms of said inhibitor per square centimeter of skin.

4. The process as claimed in claim 1 in which said inhibitor is a 3,5-disubstituted-4,5-dihydroisoxazole.

5. The process as claimed in claim 4 in which said inhibitor is 5-(N-benzyloxycarbonyl-L-para-tyrosinamidomethyl)-3-bromo -4,5-dihydroisoxazole.

6. The process as claimed in claim 5 in which said inhibitor is 5-(N-2-(s)-6-methoxy-2-naphthyl) -propionyl)-L-p-tyrosinamidomethyl-5-(s)-3-bromo-4,5-dihydroisoxazole.

* * * * *

UNITED STATES PATENT AND TRADEMARK OFFICE
CERTIFICATE OF CORRECTION

PATENT NO. : 5,143,925

DATED : September 1, 1992

INVENTOR(S) : Douglas Shander and Margaret G. Funkhouser

It is certified that error appears in the above-identified patent and that said Letters Patent is hereby corrected as shown below:

Col. 1, line 64; "4,885,298" should be --4,885,289--.

Signed and Sealed this

Twenty-third Day of November, 1993

Attest:

BRUCE LEHMAN

Attesting Officer

Commissioner of Patents and Trademarks